United States Patent [19]
Griffiths

[11] Patent Number: 5,320,119
[45] Date of Patent: Jun. 14, 1994

[54] SURGICAL TOOLS CLEANSING
[75] Inventor: Jerry R. Griffiths, Pembroke, Mass.
[73] Assignee: TNCO, Inc., Whitman, Mass.
[21] Appl. No.: 26,861
[22] Filed: Mar. 5, 1993
[51] Int. Cl.$^5$ ............................................. B08B 3/04
[52] U.S. Cl. .............................. 134/95.1; 134/166 C; 134/200; 134/201
[58] Field of Search ................... 134/95.1, 200, 201, 134/169 C, 166 C, 167 R

[56] References Cited
U.S. PATENT DOCUMENTS

| | | | |
|---|---|---|---|
| 2,211,892 | 8/1940 | Giese | 134/201 |
| 5,025,818 | 6/1991 | Kalar | 134/170 |
| 5,090,433 | 2/1992 | Kamaga | 134/169 C |
| 5,225,160 | 7/1993 | Sanford et al. | 134/200 |

Primary Examiner—Frankie L. Stinson
Attorney, Agent, or Firm—Jerry Cohen; Edwin H. Paul

[57] ABSTRACT

Wash package for surgical tools such as pistol grip graspers, cutters and the like with a tubular shaft, comprising a mating first section (10) and pivotably mounted second section (2), matable to form a wash enclosure around the pistol grip, and a pivotably mounted lock (30) and fluid admittance and removal conduits (51, 52), constructed for fluid pressurizing and exit through the tubular shaft.

6 Claims, 3 Drawing Sheets

SURGICAL TOOLS CLEANSING

BACKGROUND OF THE INVENTION

The present invention relates to certain aspects of cleansing of surgical tools and the like and more particularly to a strategy of such cleansing involving use of sealed wash enclosures for the hand grip sections of surgical tools (e.g. cutters, graspers, forceps, biopsy needles, punches, etc.) and more particularly microsurgery models of such tools.

During stomach/abdominal region surgery, this area of the body is expanded by pressurized gas inflation (insufflation) to enhance access to internal organs. Surgical instruments and adjuncts (cannulae, etc.) pierce the external and internal body walls in a sealed, essentially air-tight manner. One consequence of this approach is that such tools (the instruments and adjuncts) comprise narrow tubes penetrating body walls and the pressure of the insufflated area forces loose pieces of tissue into the tube. The tool cannot be sterilized and re-used until such pieces are removed. Air flushing, wire and brush (pipe-cleaner like) probes and other conventional artifacts are ineffective.

Analogous problems can occur in tools outside the area of surgery.

It is a principal object of the present invention to overcome the above problem with a practical, effective strategy.

It is a further object of the invention to provide a compact, portable means for fluid cleaning (generally water washing) of such tools using local water/drain facilities and to assure ease of insertion/removal of tools to be cleaned, ease of connection to fluid supplies/drains, accommodation of different tool sizes, avoidance of loss of parts of the package, light weight, economy and ease of manufacture as well as ease of cleanability of the package itself.

SUMMARY OF THE INVENTION

The foregoing objects are met by a strategy of enclosing a surgeon's hand grip section of such tools in a package, bringing fluid (preferably local tap pressure water) into the enclosure. The fluid enters openings of the tool grip region and runs through a long tubular section of the tool (usually enclosing an activating linkage) and exits—carrying biological tissue pieces—from a working tip distal end of the tool. The package encloses the grip section and forms a seal around the tube which preferably passes outside the package. After such cleansing water or other fluid pressure is removed and means are provided for automatic draining of the package enclosure, the package is opened and the tool is removed and ready for next steps (e.g., drying, sterilizing, preparation for storage or re-use). The package preferably comprises separable sections tied together with pivotal mountings including a first section of slab form with an edge entrance leading to an internal cradling region for a leading grip portion of a surgical tool and having an essentially fluid tight (when the tool is inserted) pass through for the leading fine diameter tubular section of the inserted tool, but leaving a trailing portion of the grip outside the enclosed part. A second section of the package is pivotally mounted to the first section and is also of slab form having an internal cradling region for the rear (trailing) portion of the inserted tool and an opening to fit over it. A third section is a U-form pivotal lock fitting over the second section, after the cutter is pivoted from an open to closed position, to lock second section to the first section in fluid sealing engagement at meeting end faces of the first and second sections.

Other objects, features and advantages will be apparent from the following detailed description of preferred embodiments taken in conjunction with the accompanying drawings in which:

DETAILED DESCRIPTION OF PREFERRED EMBODIMENTS

Figure 1:
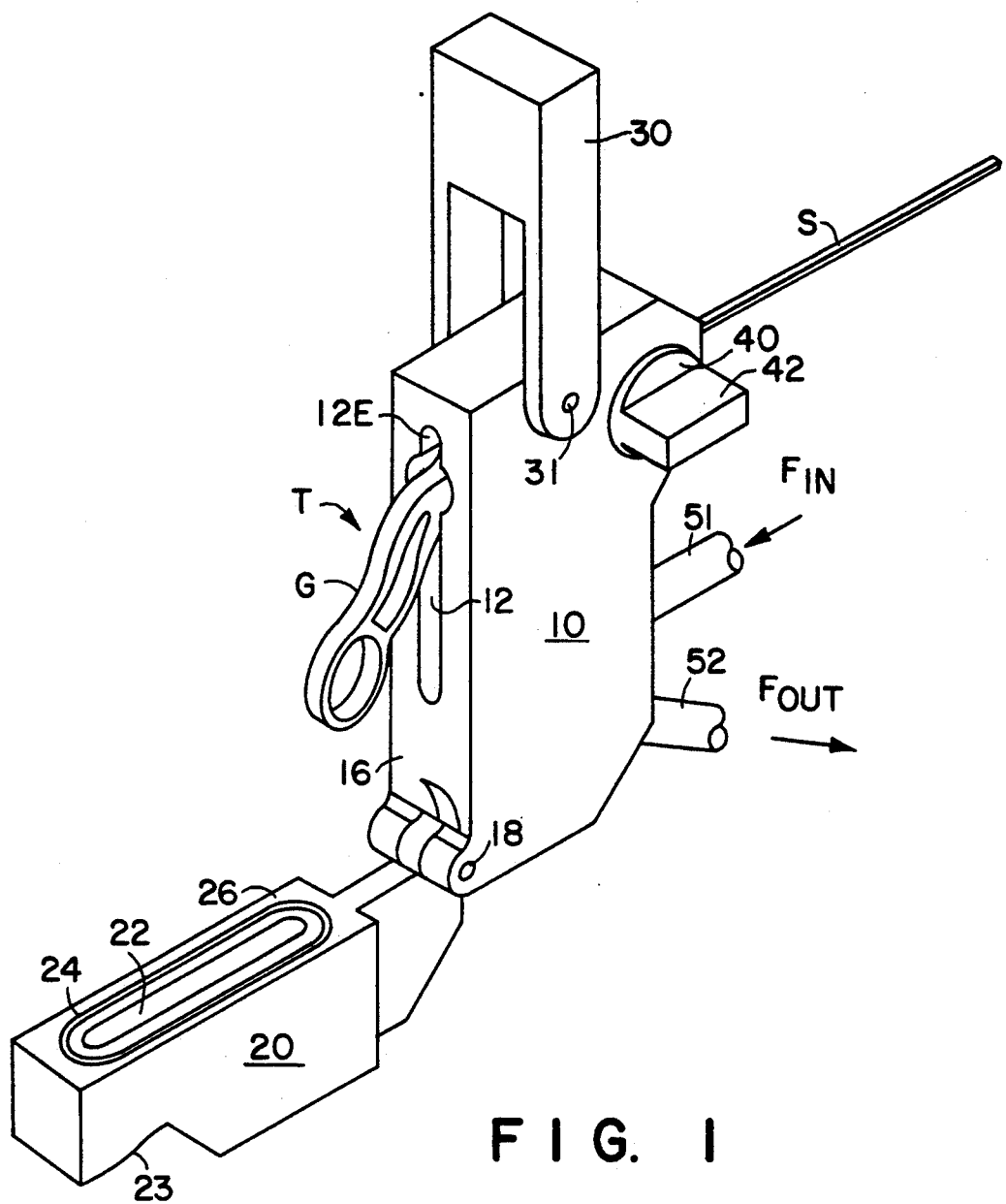
FIGS. 1 and 2 are isometric views.
Figure 2:
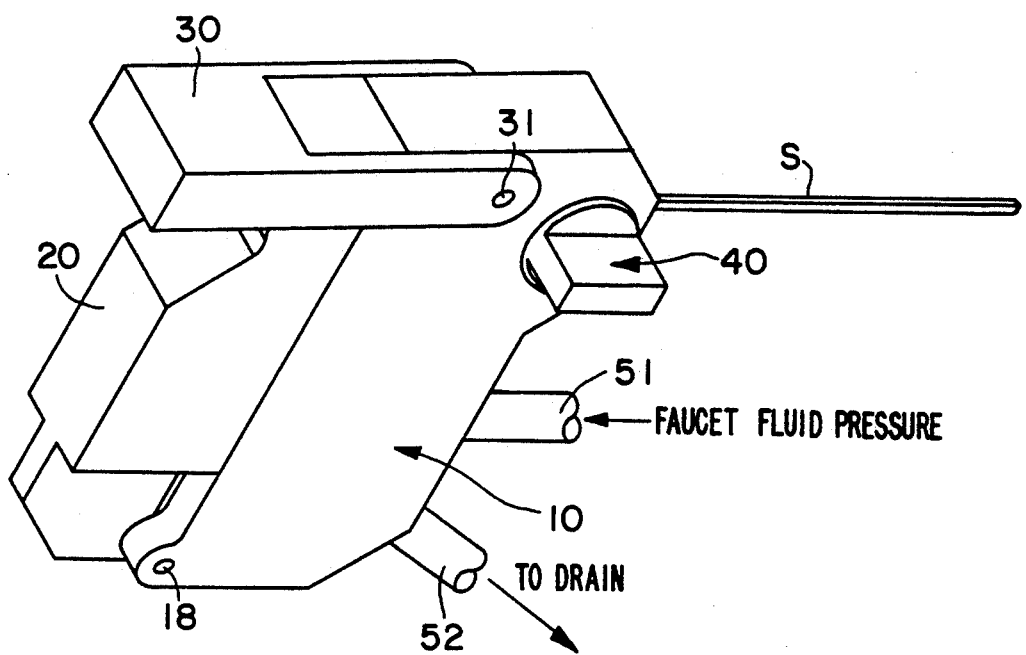
Figure 3:
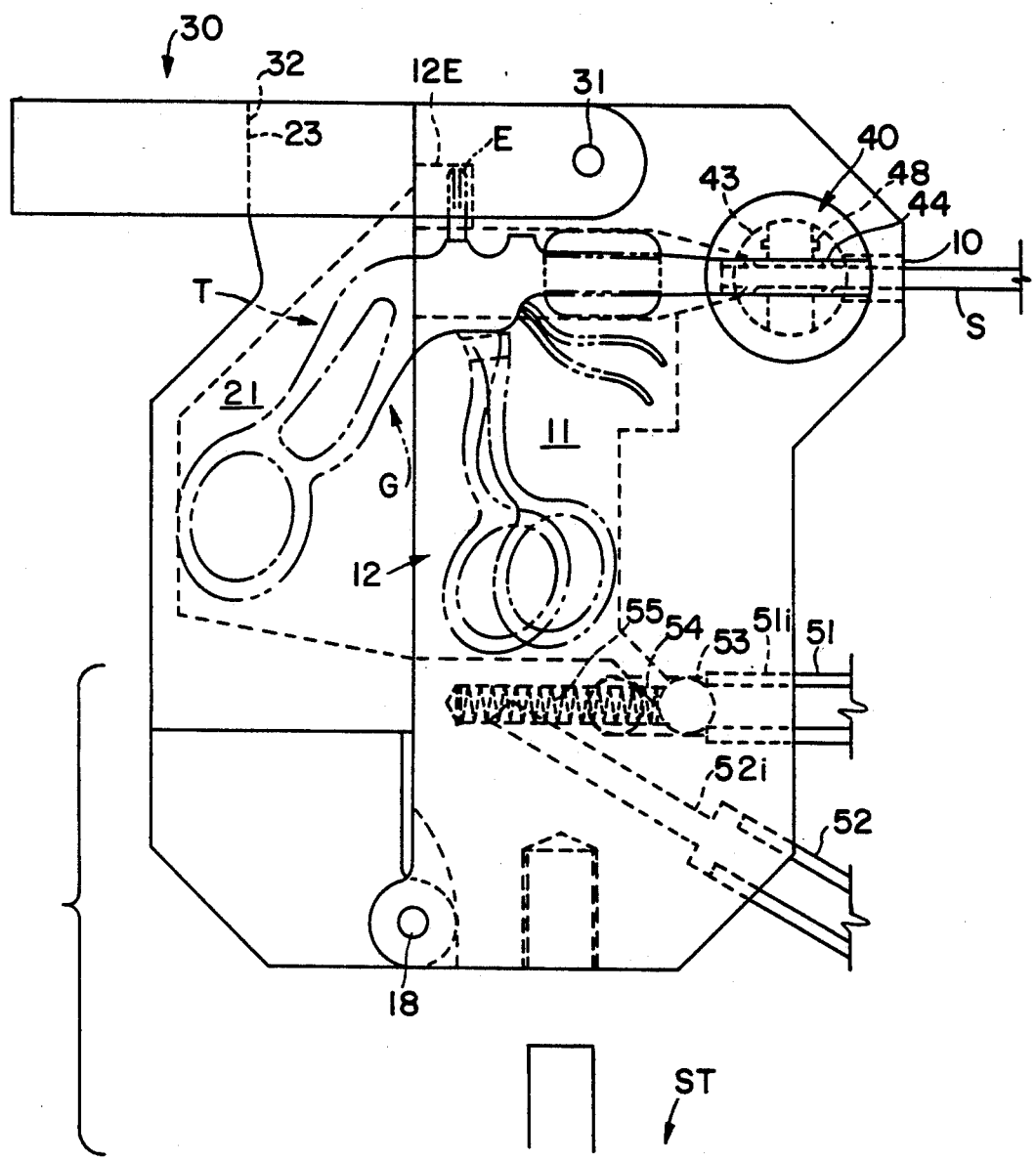
FIG. 3 is a planar view of a wash package made according to a preferred embodiment of the invention, FIG. 1 showing an open position and FIGS. 2-3 a closed position thereof.

The package comprises a first section 10 of the package of slab form which has an internal cradling region 11 (FIG. 3) including an opening 12 (FIGS. 1, 3) of keyhole form with an upper section 12E. A surgical tool T—with a bent scissors (pistol grip) form hand holding section G and an elongated shaft S with a distal, working tip (not shown)—can pass through opening 12 with the tubular shaft S leading in as the tool is inserted and emerging from section 10 via a pass-through 14 therein (FIG. 3). The section 10 has a flat entry face 16 and a pivotal mount 18 to engage and support (and retain) a second package forming section 20. The latter section has a cradle region 21 with an entrance 22, an O-ring or other sealant 24 that mounts on a flat face 26 which is engageable (upon pivoting section 20 ninety degrees from its open position of FIG. 1 to the closed positions of FIGS. 2-3) with face 16 of section 10 to form a liquid tight seal.

A locking face of cammed form is engageable by a U-form lock 30 pivotably mounted at 31 to section 10. After a tool is inserted into section 10, section 20 is swung up to complete full enclosure of the tool and lock 30 is swung down so that its flat face 32 moves along camming surface 23 of section 20 to apply sealing pressure to seal 24.

A pass-through selection assembly 40 comprises a switch 42 controlling rotation of a barrel 43 that contains, e.g., two pass-through conduits 44, 46 of different sizes, either of which can be selected to match various tools T with different tubular shafts diameters. Such assemblies can include more than two sizes and comprise e.g. linear movement means for selection rather than the rotary selection means shown. Further, such assemblies can be designed with flexible or flap seals or allow insertion of gaskets or other seals to accommodate a wider range of sizes and/or geometry of such shafts automatically or by manual adjustment.

A liquid feed pipe 51 and liquid removal pipe 52 are formed as permanent or detachable extensions of section 10 and internal parts 51$i$ and 52$i$ of said pipes lead to enclosure 11/21. A ball valve 53 with a spring back-up 54 in a well 55, i.e. a check valve, retracts under applied liquid pressure to enable fill and block drainage of the enclosure. During connection of the enclosure to incoming liquid pressure, the only escape path for the liquid is entry into the tool in one or more natural openings in the grip region, coursing through the tubular shaft and exiting through the distal shaft region near the working tip and in doing so carrying out lodged tissue pieces from within the tubular shaft. Ordinary faucet tap pressure in combination with tubular shaft (internal area) dimensions, has been found sufficient. for this purposes. Shortly after the liquid appears to run free out of the tip region, the cleansing can be stopped by cutting off the liquid supply. Upon termination of incoming liquid pressure, the check valve shifts to allow the liquid to be removed via pumping or gravity. The sections 30, 20 are pivoted to open position of FIG. 1 and the tool is removed.

The package parts can be made of a variety of materials including plastics, metals, etc., but is preferrably formed of thin section (but rigid under enclosure pressurizing conditions) aluminum or stainless steel. Materials selection and/or coating of the interior walls avoids rusting or other generation of contaminants to the tools handled in the package.

It will now be apparent to those skilled in the art that other embodiments, improvements, details and uses can be made consistent with the letter and spirit of the foregoing disclosure and within the scope of this patent. which is limited only by the following claims, construed in accordance with the patent law, including the doctrine of equivalents.

What is claimed is:

1. Wash package for hand instruments of essentially hand hold section plus a tubular shaft section and a working tip section at the distal shaft hand comprising in combination:

(a) means for forming a first cradle section for insertion therein and removal therefrom of a leading portion of the hand hold portion and a port with a sealing pass-through for the shaft and tip sections so that the shaft and tip extent out of the cradle section, (b) a second complementary cradle section for the trailing portion of the hand hold section mountable in sealing relation to the first cradle section to form a complete enclosure of the hand hold portion of the instrument, (c) means for locking the two cradle sections in sealing engagement, (d) means for selectively admitting fluid to the enclosure to fill and pressurize it and to remove fluid therefrom and for limiting fluid exit to passage through the tubular shaft and emergence from the tip to dislodge any particles in the instrument, the entire package having a size allowing handling in a variety of common sinks or the like and in form to utilize the existing fluid feed and drain facilities of such sinks or the like.

2. The package of claim 1 wherein said first cradle section incorporates fluid feed and removal passages passing from outside the package to the enclosure and wherein the means for forming first and second sections are loosely attached and mounted for moving into engagement and disenablement and clearance (for tool insertion or removal) without being entirely separated in either of such modes and the means for locking comprise a link loosely attached to one or both of said sections so as to never be entirely separated therefrom in either of such modes.

3. The package of claim 2 wherein the means forming the first and second sections are pivotably coupled and the means for locking are pivotably coupled to one of said first section forming means and comprise a pivotably movable lock, and a mating locking region of the means forming said second section.

4. The package of claim 3 wherein said locking means comprise a locking face of cam form at an interface of the second cradle section and said pivotable locking means.

5. The package of claim 3 wherein said means for selectively admitting fluid comprises a single check valve means effective to prevent drainage only when the enclosure is being pressurized from an external fluid source.

6. The package of claim 1 wherein the means forming the first section comprise multiple selective pass throughs at a single location and means for selecting one to match an inserted tool shaft.

* * * * *